(12) United States Patent
Solaun et al.

(10) Patent No.: US 12,220,131 B2
(45) Date of Patent: Feb. 11, 2025

(54) DELIVERY AND DETACHMENT SYSTEM IMPOSING A FRICTION FORCE ON A SECUREMENT WIRE TO MINIMIZE MOVEMENT OF AN IMPLANTABLE INTRAVASCULAR DEVICE

(71) Applicant: DePuy Synthes Products, Inc., Raynham, MA (US)

(72) Inventors: Daniel Solaun, Miami, FL (US);
Francisco Ales, Miami, FL (US);
David Blumenstyk, Miami, FL (US);
Zhixian Chen, Miami, FL (US);
Thomas Gallerani, Miami, FL (US);
Tyson Montidoro, Miami, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 408 days.

(21) Appl. No.: 17/569,620

(22) Filed: Jan. 6, 2022

(65) Prior Publication Data
US 2023/0210536 A1    Jul. 6, 2023

(51) Int. Cl.
*A61B 17/12* (2006.01)
*A61B 17/00* (2006.01)
*B29D 23/00* (2006.01)

(52) U.S. Cl.
CPC .......... *A61B 17/1214* (2013.01); *B29D 23/00* (2013.01); *A61B 2017/00526* (2013.01); *A61B 2017/12054* (2013.01)

(58) Field of Classification Search
CPC ...... A61B 17/1214; A61B 2017/12054; A61B 2017/00526; B29D 23/00
See application file for complete search history.

(56) References Cited

U.S. PATENT DOCUMENTS

| 9,532,792 | B2 | 1/2017 | Galdonik et al. |
| 9,532,873 | B2 | 1/2017 | Kelley |
| 9,533,344 | B2 | 1/2017 | Monetti et al. |

(Continued)

OTHER PUBLICATIONS

Co-owned, copending U.S. Appl. No. 17/569,632, filed Jan. 6, 2022.

(Continued)

*Primary Examiner* — Katherine H Schwiker
*Assistant Examiner* — Zehra Jaffri
(74) *Attorney, Agent, or Firm* — Troutman Pepper Locke LLP (57) ABSTRACT

Delivery and detachment system for an implantable intravascular device, the system including a securement wire in a passageway of an inner support tube. Imposed on the securement wire is a controlled friction force established within an intentional friction zone created by: (i) reflow of an outer sleeve through side port opening(s) in the inner support tube and into the passageway; or (ii) the securement wire having bend(s) creating an associated point(s) of direct physical contact with the inner wall of the inner support tube. During delivery of the implantable intravascular treatment device to a target site, the imposed controlled friction force minimizing movement of the securement wire relative to the inner support tube, and upon reaching the target site, a force being applied to overcome the imparted controlled friction force and releasing the implantable intravascular device.

12 Claims, 10 Drawing Sheets

(56) References Cited

U.S. PATENT DOCUMENTS

| | | | |
|---|---|---|---|
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 11,457,922 B2 | 10/2022 | Montidoro et al. |
| 2008/0306504 A1 | 12/2008 | Win et al. |
| 2010/0016837 A1* | 1/2010 | Howat ............... A61M 25/005 156/143 |
| 2011/0060360 A1 | 3/2011 | Mitelberg et al. |
| 2015/0057698 A1 | 2/2015 | Lagodzki et al. |
| 2015/0119859 A1* | 4/2015 | Cajamarca ........ A61M 25/0054 604/526 |
| 2015/0216688 A1 | 8/2015 | Landsman et al. |
| 2016/0317220 A1* | 11/2016 | Guo .................. A61B 18/1492 |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0028778 A1* | 2/2018 | Dillon ................. A61B 1/0051 |
| 2018/0304040 A1* | 10/2018 | Jalgaonkar ........ A61M 25/0054 |
| 2020/0229957 A1 | 7/2020 | Bardsley et al. |
| 2020/0306501 A1* | 10/2020 | Yee .................... A61M 25/0051 |
| 2021/0085498 A1 | 3/2021 | Nygaard et al. |

OTHER PUBLICATIONS

European Search Report in counterpart European Patent Application No. 23150411.9-1122 (May 19, 2023)(12pp.).

* cited by examiner

DELIVERY AND DETACHMENT SYSTEM IMPOSING A FRICTION FORCE ON A SECUREMENT WIRE TO MINIMIZE MOVEMENT OF AN IMPLANTABLE INTRAVASCULAR DEVICE

FIELD OF THE INVENTION

The present invention relates to a system for delivery and detachment of an implantable intravascular device used during an endovascular treatment or procedure. In particular, the present invention is directed to a delivery and deployment system including an inner support tube having a passageway in an axial direction with a securement wire threaded therethrough. During delivery of the implantable intravascular device to a target site in the body, movement of the securement wire within the passageway of the inner support tube of the delivery and detachment system is minimized or prevented via an intentional friction zone.

DESCRIPTION OF RELATED ART

Implantable intravascular devices are commonly used in endovascular procedures or treatments of various vascular ailments, for example, brain aneurysms. A catheter is inserted into the femoral artery in patient's leg and guided by imaging navigated through the vessel to the target site in the brain where the aneurysm is located. With the distal end of the catheter properly positioned on a proximal side of the aneurysm, a microcatheter is tracked through the catheter to the proximal side of the aneurysm. A delivery and deployment system loaded with an implantable intravascular device (e.g., embolic coil) is introduced via the microcatheter to the target site. During delivery to the target site, the implantable intravascular device is mechanically secured within the delivery system, typically via a wire (e.g., securement wire or pull wire). When properly positioned at the target site (e.g., at the location of the aneurysm) the wire is severed releasing the implantable intravascular device (e.g., embolic coil) to be deposited within the aneurysm. Severing of the embolic coil from the securement wire is typically achieved by passing of a small electrical current through the wire. This process is repeated until the area of the vessel with the weakened wall is tightly packed with numerous embolic coils occluding blow flow thereto thereby preventing rupture.

During delivery of an implantable intravascular device to a target site within the artery or vessel, conventional delivery and detachment systems are designed such that no friction force is intentionally imposed on the securement wire extending therethrough. It is the goal and intent of such conventional devices to avoid altogether imposing any friction force on the securement wire. An issue or drawback associated with such conventional friction-free configuration is that during delivery the securement wire is subject to unwanted shifting, movement, or translation resulting in potential imprecise delivery or detachment of the implantable intravascular device at the target site in the artery.

It is therefore desirable to develop an improved system for delivery and detachment of an implantable intravascular device that intentionally introduces a controlled amount of friction force on the securement wire to minimize or prevent unwanted shifting, movement, or translation during delivery of the implantable intravascular device to the target site in the artery.

SUMMARY OF THE INVENTION

The present invention is directed to an improved system for delivery and detachment of an implantable intravascular device that intentionally introduces a controlled amount of friction force on the securement wire to minimize or prevent unwanted shifting, movement, or translation during delivery of the implantable intravascular device to the target site in the artery.

Another aspect of the present invention relates to a delivery and detachment system for an implantable intravascular device, in which the system includes an inner support tube having a passageway extending in an axial direction from a proximal end to an opposite distal end. The system further includes a securement wire extending through the passageway of the inner support tube. Imposed on the securement wire is a controlled friction force established within an intentional friction zone located anywhere between the distal end of the inner support tube and a midway point between the respective proximal and distal ends of the inner support tube.

Yet another aspect of the invention is directed to a method for manufacture of a delivery and detachment system for an implantable intravascular device, as described in the preceding paragraph. Initially, an inner support tube having a passageway extending in an axial direction from a proximal end to an opposite distal end is provided. Then, a securement wire is threaded through the passageway of the inner support tube, imposing on the securement wire a controlled friction force established within an intentional friction zone located anywhere between the distal end of the inner support tube and a midway point between the respective proximal and distal ends of the inner support tube.

While still another aspect of the present invention relates to a method of using a delivery and detachment system for an implantable intravascular treatment device. The delivery and detachment system including an inner support tube having a passageway extending in an axial direction between a proximal end and an opposite distal end; and the delivery; and detachment system further including a securement wire extending through the passageway of the inner support tube; imposed on the securement wire is a controlled friction force established within an intentional friction zone located anywhere between the distal end of the inner support tube and a midway point between the respective proximal and distal ends of the inner support tube. The method of using the system being that during delivery of the implantable intravascular treatment device to a target site, the imposed controlled friction force minimizes movement of the securement wire relative to the inner support tube. Whereas, upon the implantable intravascular treatment device reaching the target site, a force is applied in a proximal direction on the securement wire sufficient to exceed the imparted controlled friction force and releasing the implantable intravascular device from the delivery and detachment system.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which.

DETAILED DESCRIPTION OF THE INVENTION

In the description, the terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionist. The terms "occlusion", "clot" or "blockage" are used interchangeably.

During an endovascular treatment procedure (e.g., coil embolization), it is desirable for the system to reliably deliver and detach/deploy/deposit/release the implantable intravascular device (e.g., embolic coil) at a precise location or target site (e.g., aneurysm) within a vessel or artery. The implantable intravascular device (e.g., embolic coil) is releasably loaded on (e.g., secured to) the distal end of a delivery and detachment system that together as a unit are advanced to the desired target site in the vessel or artery. Releasable securement of the implantable intravascular device is via a securement wire (e.g., pull-wire) extending axially in a proximal direction through the delivery and detachment system. When the implantable intravascular device is precisely located at the target site in the artery or vessel the interventionalist applies sufficient force in a proximal direction on the securement wire to release (e.g., disengage) the implantable intravascular device for deposit at that location within the artery. Any shifting, translation, or movement of the securement wire during delivery of the implantable intravascular device may result in imprecise positioning and depositing offset from the intended target site in the artery or vessel.

The present inventive delivery system minimizes or prevents unwanted translation, shifting, or movement of the securement wire during delivery of the implantable intravascular device to the target site in the artery by intentionally introducing or imposing a controlled friction force on the securement wire within an intentional friction zone.

Figure 1:
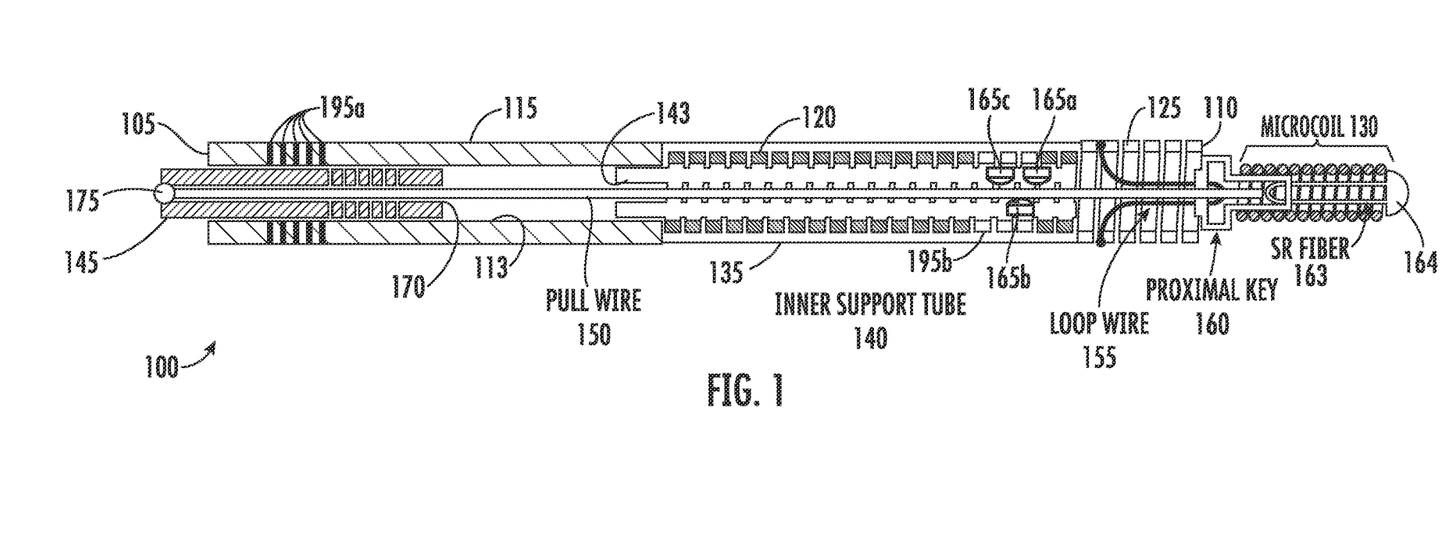
FIG. 1 is a longitudinal/axial cross-sectional view of an exemplary assembled system for delivery and detachment of an implantable intravascular device (e.g., embolic coil) in accordance with the present invention including an inner support tube having an intentional friction zone created along a distal section of an internal wall of a longitudinal/axial passageway defined therethrough with which a straight securement wire directly physically contacts or directly physically engages at multiple points.

FIG. 1 is a longitudinal/axial cross-sectional view of an exemplary assembled delivery and detachment system 100 in accordance with the present invention with an implantable intravascular device (e.g., embolic coil) 130 loaded thereto. Delivery and detachment system 100 has a proximal end 105 and an opposite distal end 110 to which the implantable intravascular device (e.g., embolic coil) 130 is releasably secured thereto. System 100 includes a main or outer delivery tube 115 having a channel 113 extending in a longitudinal/axial direction therethrough. Insertable into the distal end of the channel 113 of the main delivery tube 115 is a proximal end of an inner support tube 140 which itself has a passageway 143 defined therethrough in a longitudinal/axial direction. A coil 120 (e.g., a helical coil) is disposed radially outward of the outer surface of the inner support tube 140. An outer sleeve 135, preferably made of a lubricious reflowable material or a reflowable material having a lubricious outer coating, covers the outer surface of the coil 120. By way of example, the outer sleeve is a thermoplastic elastomer (TPE) such as a polyether block amide (PEBA) known under the tradename of PEBAX®. In a preferred embodiment, at the distal end 110 of the delivery and detachment system 100 is disposed a compressible component (e.g., a helical detachment coil) 125 having an outer diameter larger than the coil body 120, wherein the outer sleeve 135 stops proximally of (does not extend in an axial direction over or cover any portion of the compressible component 125). Similarly, the inner support tube 140 terminates proximally (i.e., does not extend into the cavity) of the compressible component 125.

An implantable intravascular device (e.g., embolic coil) 130 is releasably connected to the distal end 110 of the delivery and detachment system 100 via a loop wire 155 threaded through an engagement device (e.g., proximal key) 160 disposed between the distal end of the compressible component 125 and the proximal end of the implantable intravascular device 130. Respective free proximal ends of the loop wire 155 are permanently affixed to an inner surface of the compressible component 125, whereas an opposite distal end of loop wire 155 forms a closed loop. Engagement component (e.g., proximal key) 160 has an opening. As such, the implantable intravascular device 130 is releasably attached, connected, or secured to the distal end 110 of the delivery and detachment system 100 by bending a portion of the closed loop distal end of the loop wire 155 upwards (e.g., perpendicularly to the axial direction of the delivery and detachment system) through the opening of the engagement component 160 and threading the distal end of the securement wire (e.g., pull wire) 150 in a distal direction through the bent upwards closed loop distal end of the loop wire 155. Securement wire 150 is depicted as straight (i.e., extending or moving uniformly in one direction only; without a curve, kink, or bend); however, a non-straight, curved, kinked, or bent securement wire is possible to impart an even greater friction force. Engagement of the distal end of the securement wire 150 within the closed loop distal end of the loop wire 155 secures the engagement component (e.g., proximal key) 160 and implantable intravascular device (e.g., embolic coil) 130 attached distally thereto to the distal end of the delivery and detachment system 100.

The implantable intravascular device 130 is deployed, released, or deposited at a target site in the artery by subjecting the securement wire 150 to an axial force in a proximal direction (e.g., pulling in a proximal direction). Sufficient axial force is applied in the proximal direction so that the distal end of the securement wire 150 is disengaged (i.e., free from, clear of, or no longer constrained by) the loop wire 155. Now released from the loop wire 155, the securement wire 150 is no longer connected to the engagement component (e.g., proximal key) 160 or implantable intravascular device 130 attached thereto.

Compressible component 125 may initially be under compression subject to decompression/expansion once the securement wire 150 is disengaged from the loop wire 155 imparting a force in a distal direction on the proximal end of the implantable intravascular device (e.g., embolic coil) 130. The loop wire 155 preferably has sufficient flexibility such that when the decompression/expansion force is imparted by the compressible component 125 the loop wire 155 moves out of the opening of the engagement component (e.g., proximal key) 160 thereby detaching/releasing the implantable intravascular device 130 from the delivery system 100. Moreover, the force imparted by the compressible component 125 during decompression/expansion preferably pushes the implantable intravascular device 130 in a distal direction away from the distal end 110 of the delivery system 100 creating a predetermined separation distance therebetween upon deployment. Other purely mechanical (non-thermal and non-electrical) arrangements releasable upon application of an axial force in a proximal direction (e.g., pulling force) are contemplated and within the intended scope of the present invention for releasably securing the implantable intravascular device to the distal end of the delivery and detachment system.

A stretch resistant element 163 is preferably disposed internally within the cavity of the implantable intravascular device 130. At a distal end, stretch resistant element 163 is secured via a bead or other stopping component 164 having an outer diameter that prevents passage in a proximal direction into the interior cavity of the implantable intravascular device 130, while its opposite proximal end is secured to the distal end of the engagement component 160 (e.g., threaded through an opening thereof).

For trackability during use one or more marker bands detectable through imaging may be provided along regions of one or more components of the delivery and detachment system. For instance, marker bands 195a, 195b (e.g., a fluor-saver marker) may be disposed along an outer surface of a proximal section of the main delivery tube 115 and a distal section of the coil body 120 (preferably aligned with that of the side port openings 165a, 165b, 165c created in the inner support tube 140). The arrangement, number, and use altogether of marker bands is optional.

In preparation of assembly of the components of the present inventive delivery and detachment system 100, along a distal section of the inner support tube 140 a plurality of radially inward cuts are made extending from the outer surface through to (intersecting) the passageway 143 creating a plurality of side port openings 165 that allow a fluid (e.g., the reflowable material of the outer sleeve) to flow/seep therethrough. The term "distal section" is expressly defined as any section, region, portion, or area along the inner support tube that satisfies the following conditions: (i) in a distal direction relative to a midpoint between opposing proximal and distal ends/tips of the inner support tube; and (ii) in a proximal direction relative to the distal end/tip of the inner support tube. In other words, the selected distal section along which the intentional friction zone is created is located anywhere in a region between, without including either, the distal end/tip and the midpoint of the inner support tube.

Figure 3A:
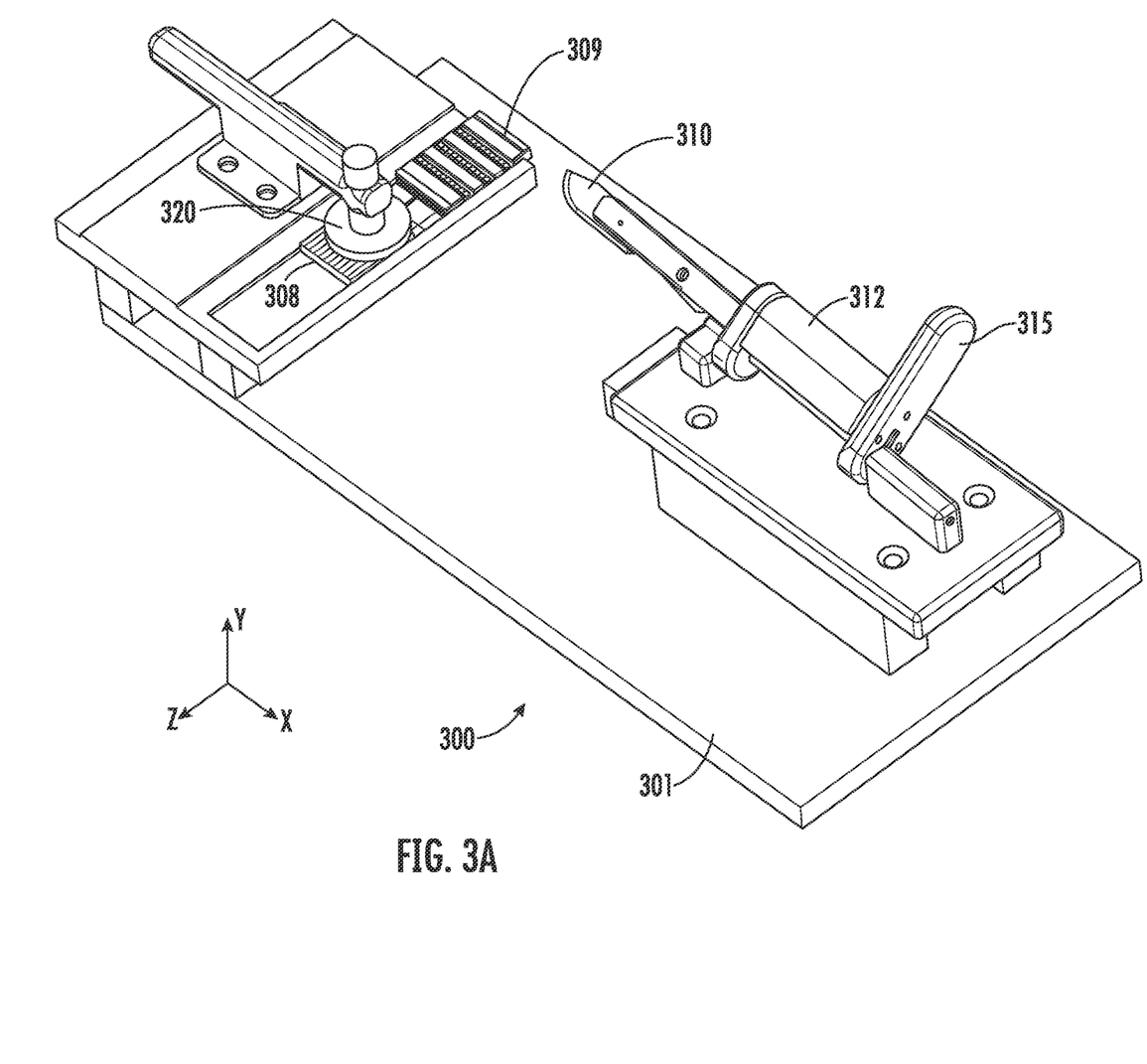
FIG. 3A is a perspective view of an exemplary supporting and cutting structure for creating the radially inward side port openings in the inner support tube of FIG. 2A.
Figure 3B:
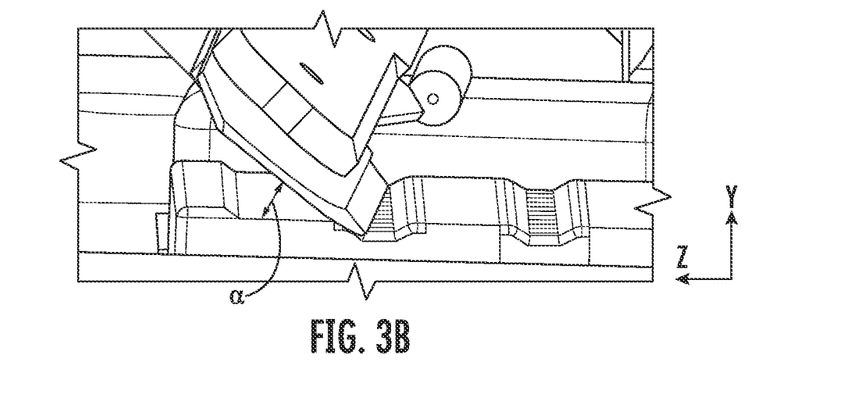
FIG. 3B is an enlarged view parallel to the Z-axis of the blade of FIG. 3A making a first skived cut of one side port opening in the inner support tube.
Figure 3C:
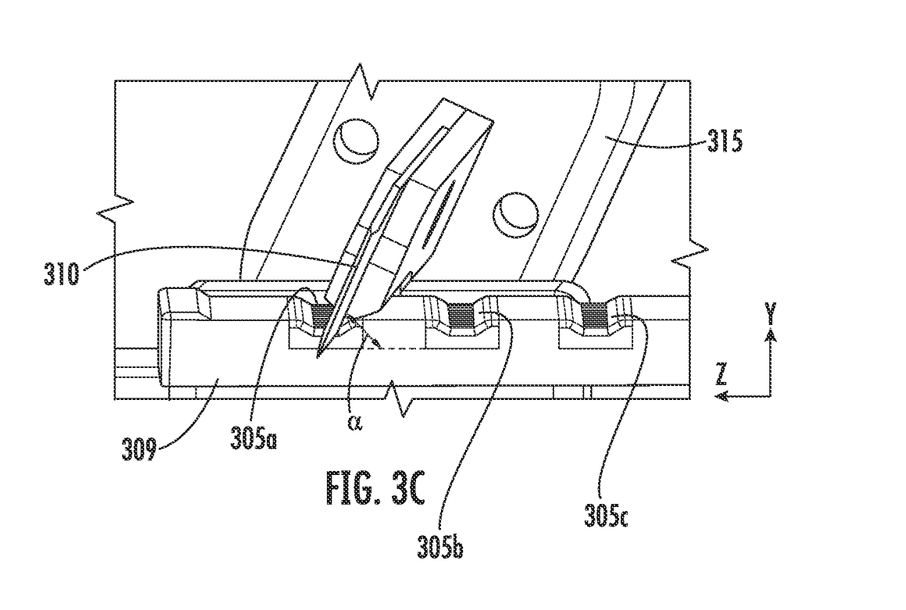
FIG. 3C is an enlarged view parallel to the Z-axis of the blade (flipped 180° relative to the first skived cut of FIG. 3B) making a second skived cut to complete the formation of the one side port opening in the inner support tube.
Figure 3D:
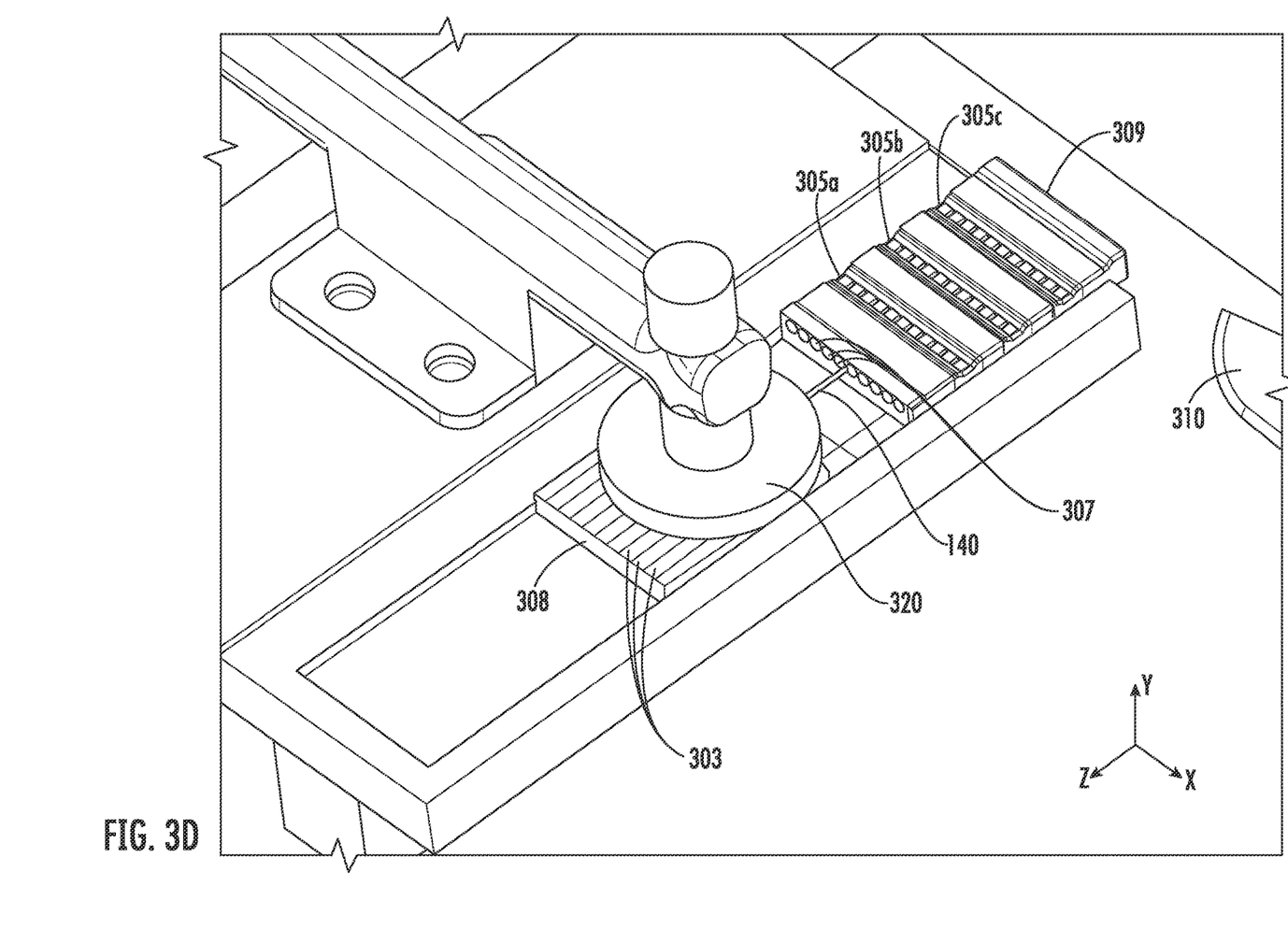
FIG. 3D is an enlarged view of the inner support tube supported by a corrugated/wave shape platform and side port template of the supporting and cutting structure of FIG. 3A while being secured in position via a clamp.

FIG. 3A is a perspective view of an exemplary supporting and cutting structure 300 used to make radially inward skived cuts into an outer surface of the inner support tube 140 through to (intersecting) the passageway 143 defined axially therein. The inner support tube 140 in which the side openings are to be created is supported on the structure 300 and held in position by a clamp 320 (FIGS. 3A & 3D).

A side port template 309 having a plurality of troughs (305a, 305b, 305c) arranged parallel to one another in an X-direction define the location, spacing, arrangement and the angle of the cuts to be made to the inner support tube 140 to create the side port openings 165 having a desired geometric cross-sectional shape (e.g., trapezoidal shape). Three troughs (305a, 305b, 305c) are shown in the example represented in FIGS. 3A & 3D all having the same cross-sectional shape (e.g., trapezoidal shape); however, the number, location, spacing, arrangement, and/or cross-sectional shape of each trough may be designed, as desired.

Figure 2A:
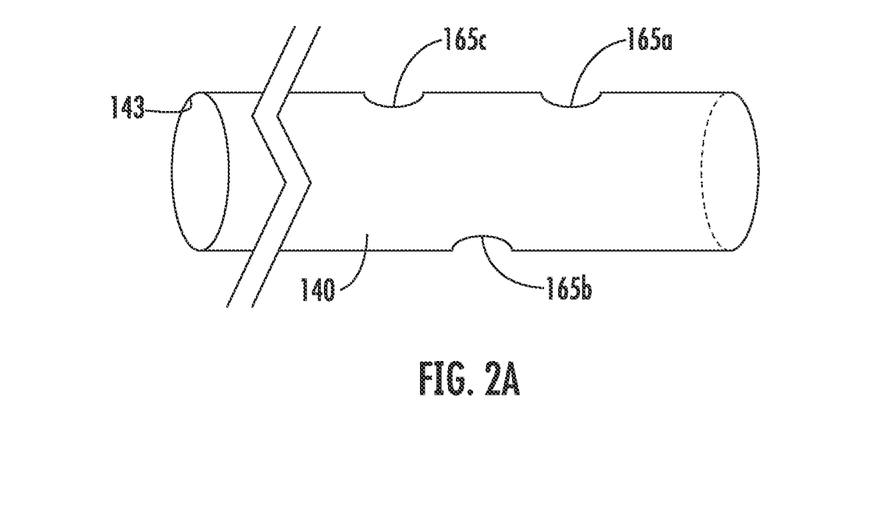
FIG. 2A is a side view of an exemplary configuration of an altered inner support tube in accordance with the present invention having a plurality of side port openings created therein along a distal section thereof.
Figure 2B:
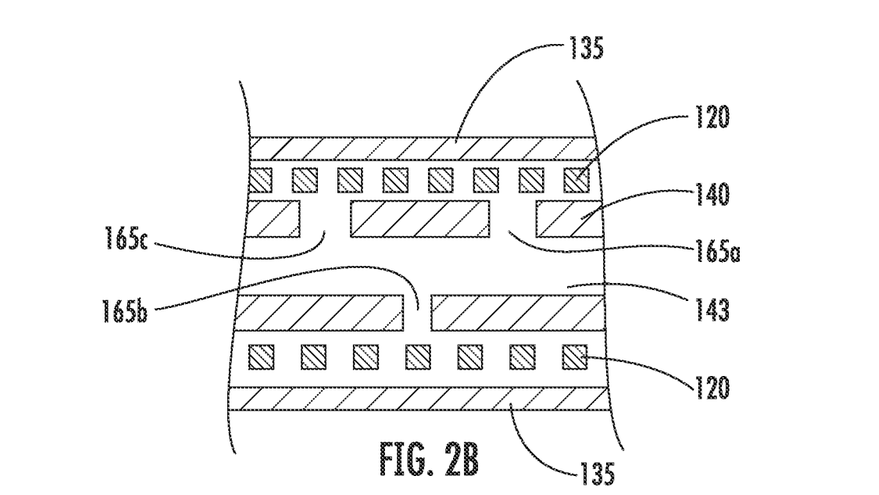
FIG. 2B is a partial longitudinal/axial cross-sectional view of the present inventive inner support tube prior to fusing of the reflowable material of the outer sleeve through the side port openings defined therein and into the longitudinal/axial passageway.
Figure 2C:
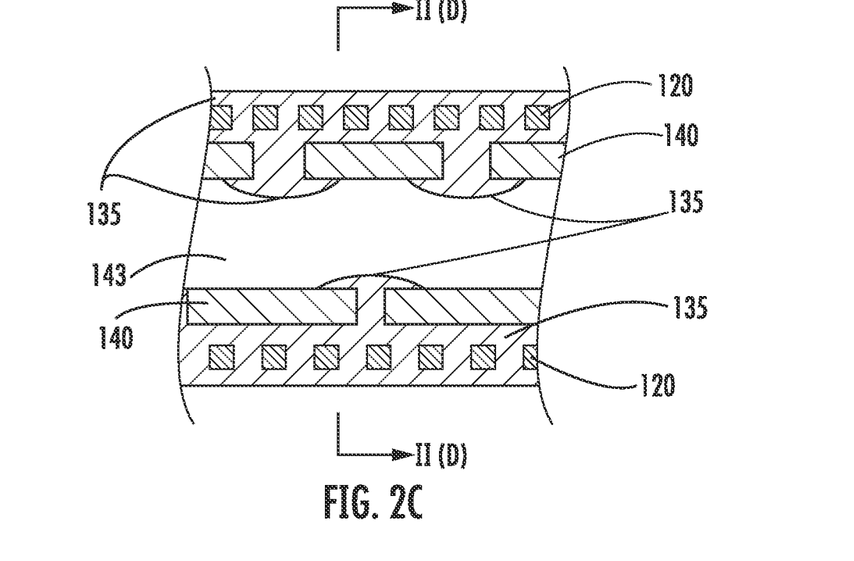
FIG. 2C is a partial longitudinal/axial cross-sectional view of the present inventive inner support tube following seepage of the reflowable material of the outer sleeve through the side port openings and into the longitudinal/axial passageway thereby at those locations reducing the inner diameter and creating a friction zone along a distal section thereof.
Figure 2D:
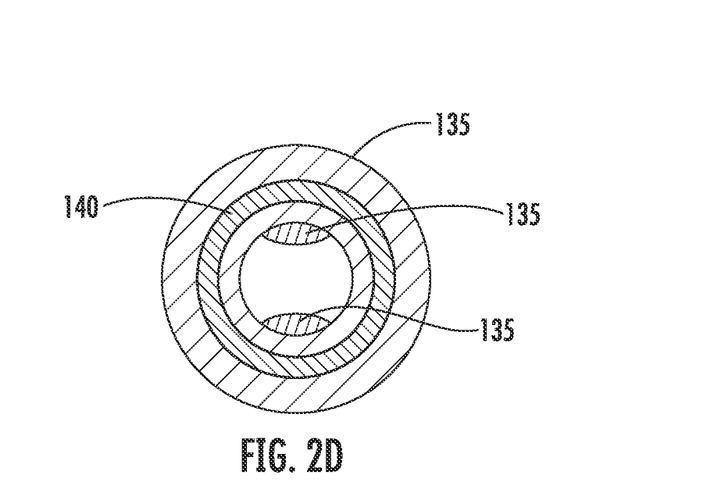
FIG. 2D is a radial cross-sectional view along lines II(D)-II(D) of FIG. 2C showing the reflowable material of the outer sleeve seeped partially into the passageway of the inner support tube.

By way of example, adjacent side port openings defined in the inner support tube 140 depicted in FIG. 2A are separated from one another both in a longitudinal/axial direction and in a radial direction. That is, side port 165a is separated both in a longitudinal/axial direction and a radial direction (approximately 180°) relative to that of adjacent side port 165b, as is true for all adjacent side port openings illustrated. Three side port openings 165a-165c are illustrated in FIG. 2A; however, any number of two or more side port openings may be made, as desired. The geometric shape of each side port opening may be modified, as desired, so long as each side port opening extends radially inward through the inner support tube 140 (i.e., from its outer surface to its passageway 143). A controlled amount of intentionally introduced friction force imposed on the securement wire 150 when threaded through the passageway 143 is produced by selecting: (i) the number of side port openings; (ii) the location and arrangement of the side port openings (both longitudinally/axially and radially); and (iii) the dimensions in an axial direction (Z-direction) and in a radial direction (X-direction) of each side port opening created in the inner support tube.

Figure 6A:
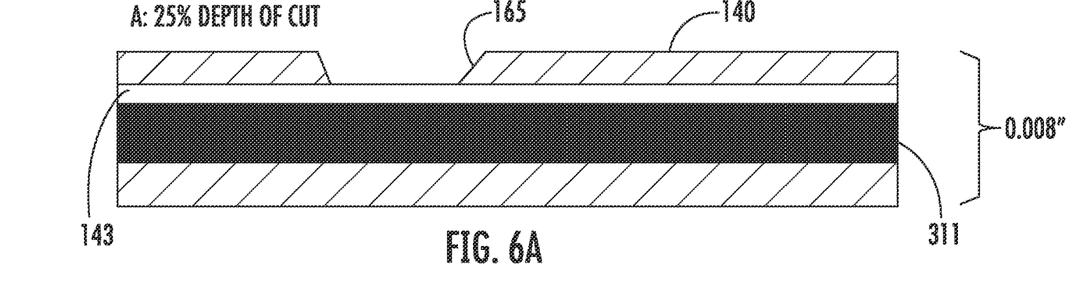
FIGS. 6A & 6B illustrates a longitudinal cut away view and bottom portion end view, respectively, of a section of an exemplary inner support tube with a protective wire inserted into the passageway thereof, wherein the inner support tube has defined therein a single side port opening at a 25% depth (radially inward) cut.
Figure 6B:
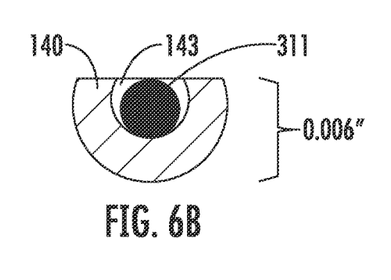
Figure 6C:
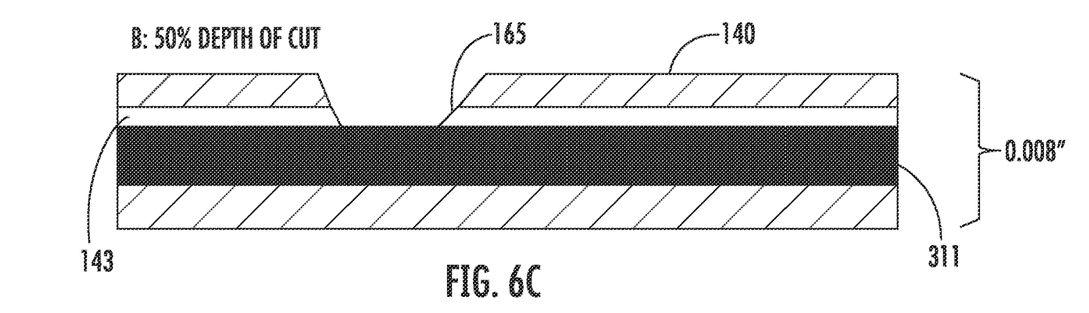
FIGS. 6C & 6D illustrates a longitudinal cut away view and bottom portion end view, respectively, of a section of an exemplary inner support tube with a protective wire inserted into the passageway thereof, wherein the inner support tube has defined therein a single side port opening at a 50% depth (radially inward) cut.
Figure 6D:
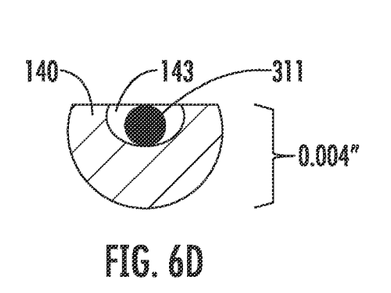

In the exemplary configuration of FIG. 2A, each side port opening of the inner support tube has an axial length of approximately 1 mm, with at least approximately 1 mm separation in an axial direction between adjacent side port openings. Continuing with this example, at a minimum there would be approximately 2 mm distance in an axial direction from the proximal end of the first side port opening and the proximal end of the adjacent/next second side port opening. The spacing of cuts in a radial direction may be more compact depending on such factors as the depth (radially inward) of the cut and amount of remaining material (i.e., strength) of the inner support tube. Referring to FIGS. 6A-6D varying exemplary depth cuts are made to the inner support tube. Specifically, FIGS. 6A & 6B depict a longitudinal cut-away view and a bottom portion end view, respectively, of the inner support tube 140 having a side port opening 165 with a 25% depth (radially inward) cut, whereas FIGS. 6C & 6D depict the same views for a side port opening with a 50% depth (radially inward) cut. The deeper radial cut (50% depth) extending further radially inward into the clearance or free space within the passageway 143 of the inner support tube 140 when a smaller diameter protective metal wire/mandrel 311 is used.

Prior to assembling the delivery and detachment system, the inner support tube is mechanically supported (held in place) on a supporting and cutting structure while the plurality of radially inward cuts are made to create the side port openings along the distal section thereof. FIGS. 3A & 3D depict an exemplary supporting and cutting device 300 including a substrate 301 and a corrugated/wave platform 308 having a plurality of longitudinally arranged parallel ridges and valleys 303 extending along the Z-axis. The inner support tube 140 in which the side port openings are to be created is placed within an associated one of the valleys (between adjacent ridges) 303 of the corrugated/wave platform 308 so that the longitudinal axis of the inner support tube 140 is arranged parallel with the Z-axis. Side port openings in more than one inner support tube may be cut simultaneously at the same time, wherein each inner support tube 140 is placed within an associated valley 303 on the corrugated/wave platform 308 of the supporting and cutting device 300. Supporting and cutting device 300 further includes a side port template 309 having defined therein parallel to the Z-axis a series of channels 307 equal in number to that of the valleys 303 of the corrugated/wave platform 308. Each channel 307 of the side port template 309 is aligned in a Z-direction with a corresponding valley 303 of the corrugated/wave platform 308.

Side port template 309 has a plurality of troughs (e.g., recesses) 305a-305c defined therein parallel to one another and extending along an X-axis perpendicular to the Z-axis. The number of troughs 305a-305c corresponds to the desired number of side port openings to be created in the inner support tube. Each trough 305a, 305b, 305c preferably, but need not necessarily, has the same cross-section parallel to the Z-axis. The channels 307 defined in the side port template 309 parallel with the Z-axis emerge on one side, extend across, and thereafter continue on the opposite side of each of the plurality of troughs 305a-305c. Each trough preferably has a trapezoidal like cross-sectional shape parallel to the Z-axis (i.e., tapered sides widening in opposing directions from a flat bottom surface) connecting the narrowing free ends of the tapered sides), as shown in FIGS. 3B & 3C. The preferred range of angularity of the tapered sides of the notch is an acute angle $\alpha$ (e.g., less than 90°) relative to the Z-axis extending perpendicularly through the channel 307.

Initially, the inner support tube 140 in which the side port openings are to be created is placed/supported within one of the valleys 303 of the corrugated/wave shape platform 308 and slid along the Z-direction into an associated channel 307 defined through the side port template 309 (FIG. 3D). With continued advancement in the Z-direction upon encountering each trough 305a the distal end of the inner support tube 140 emerges/exits from the channel 307, advances across the associated trough, and once again is received in the channel that picks up on the opposite side of the trough. After advancing across the final or last trough, the distal end of the inner support tube is preferably threaded/received once again in the channel at the opposite side of the final/last trough to ensure that the distal most end of the inner support tube is supported/held within the channel while the side port openings are being cut.

Figure 3E:
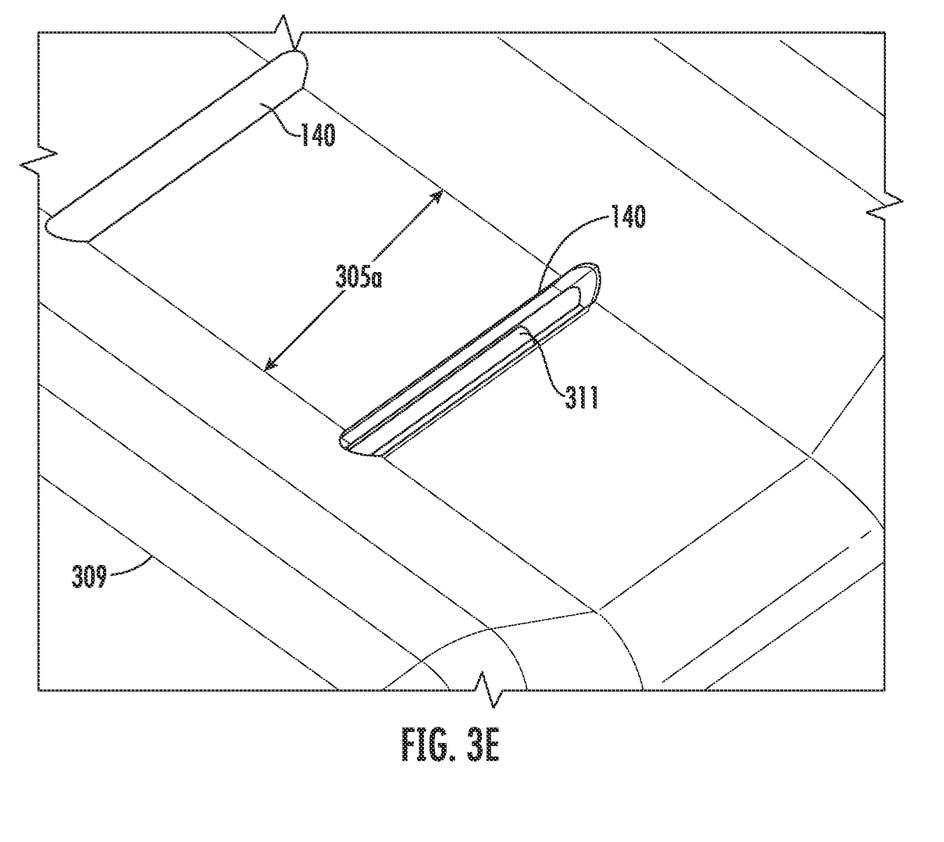
FIG. 3E is an enlarged view of two inner support tubes slid through/across associated troughs of the side port template of the supporting and cutting structure of FIG. 3A, wherein the lower inner support tube has a protective wire partially inserted through the longitudinal/axial passageway thereof.

Once fully inserted into a corresponding channel 307 of the side port template 309, the inner support tube 140 is held in position on the supporting and cutting device 300 via a clamp 320. With the inner support tube 140 secured in place on the supporting and cutting device 300, a protective wire 311 made of metal or some other material impenetrable by the blade is threaded through the passageway 143 preventing piercing/penetrating of the blade through to the opposing side (180° opposite side) of the inner support tube when making the skived cuts. FIG. 3E is an enlarged view of the inner support tube 140 extending across the trapezoidal trough 305a of the side port template 309 depicting the protective wire 311 as it is being advanced in a distal direction through the passageway 143 thereof.

A blade 310 (e.g., razor blade) is receivable within an opening in a hinged mounting arm 312 the angle of which may be adjusted, as desired, via a rotating handle 315. Preferably, the blade 310 is secured in place using a conventional locking mechanism (e.g., tightening thumb screw) at an acute angle $\alpha$ (less than 90° relative to the Z-axis), substantially conforming to the angle of the tapered sides of the trapezoidal trough. Each side port opening 165 is preferably made by two passes/cuts of the blade using the exemplary supporting and cutting device of FIG. 3A, insufficient reflow of the material reaching the passageway of the inner support tube to create the intended friction zone being achieved if only a single cut (slit) was made. A first pass/cut within one of the troughs is made with the blade 310 oriented at an acute angle $\alpha$ (less than 90° relative to the Z-axis), as shown in FIG. 3B, for each location of the side port opening. Thereafter, the rotating handle 315 is adjusted 180° (flipped horizontally) (as shown in FIG. 3C) at which position the second pass/cut is made with the blade to complete that particular side port opening. With the second pass/cut of the blade a piece (wedge) of the inner support tube bounded on either side by the respective passes/cuts is lifted or removed revealing the side port formed therein (and the now visible passageway). This process is repeated for each of the plurality of side ports desired in the distal section of the inner support tube. Referring to FIG. 3A, troughs 305a, 305c may be used to create side port openings 165a, 165c, respectively, while side port opening 165b may be created using trough 305b (after rotating the inner support tube 140 by 180°). Trapezoidal shape side cuts are preferred over a perpendicular cut relative to the X-axis to ensure that the size of the side port opening is sufficient to allow sufficient material to reflow/seep therethrough and into the passageway.

Using a blade (e.g., a razor blade, knife, or other cutting device) 310 a plurality of radially inward cuts, preferably skived cuts, are made along the distal section or region of the inner support tube 140 to create the side port openings 165a-165c. Each radially inward skived cut removes a portion of the outer surface of the inner support tube 140 through to the longitudinal/axial passageway 143 extending from its proximal end/tip to its opposite distal end/tip.

The number of side port openings and width (along the Z-axis) of each side port opening may be modified, as desired. Each side port opening may have a uniform shape and size or vary, as desired. Inner support tube 140 prevents or minimizes stretch resistance of the securement wire 150 within the delivery system 100. Thus, the shape and size of the side port opening is selected with several competing considerations in mind. On the one hand, the side port opening is sufficient in size to allow reflow/seepage of the reflowable outer sleeve material and creation of a controlled amount of friction force on the securement wire. While, on the other hand, the wider the side port opening the weaker the ability of the inner support tube to provide such resistance.

The present inventive inner support tube has been shown and described as having a plurality of side port openings defined therein with each side port opening being formed from two skived cuts. The angle of the single cut may be at any desired angle α in a range of 90° (relative to the Y-axis)≥α>0° (FIG. 3C).

Figure 3F:
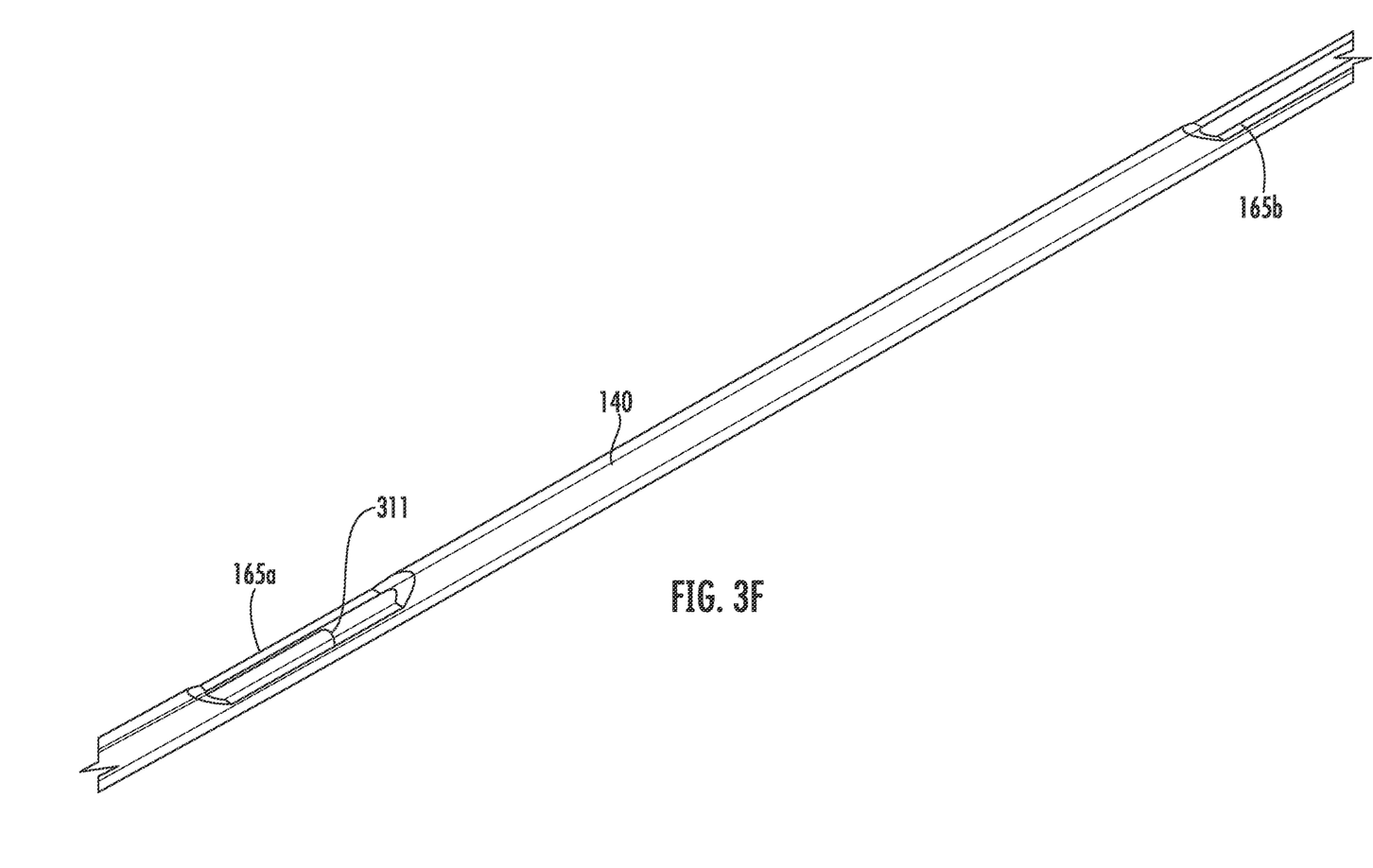
FIG. 3F is an enlarged view of the protective wire being withdrawn from the passageway of the inner support tube after the creation of the side port openings therein.
Figure 4:
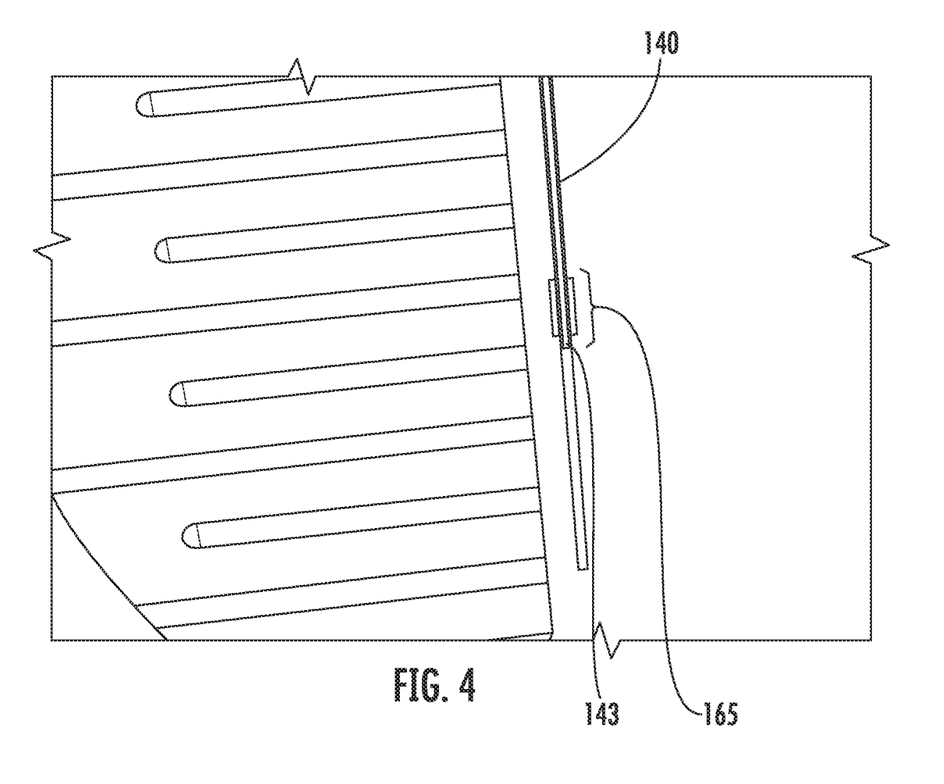
FIG. 4 depicts the inner support tube with a single radially inward side port opening defined therein exposing the passageway thereof.

With the desired number of side port openings created, following withdraw of the protective wire 311 from the passageway 143 (as illustrated in FIG. 3F), the inner support tube 140 comprising part of the present inventive delivery and detachment system is ready to be assembled. Specifically, the inner support tube 140 with the side port openings 165a, 165b, 165c defined in a distal section or region thereof is inserted into the interior cylindrical shape cavity formed by the coil 120. No portion of the inner support tube 140 extends in a longitudinal direction into the inner cavity of the compressible element 125, i.e., each of the side port openings 165 are disposed proximally of and separated a predetermined distance relative to the compressible element 125. The outer sleeve or covering 135 is positioned about or covering the outer surface of the coil 120. For illustrative purposes only, the inner support sleeve 140 is first inserted into the coil 120 which together as a unit are received within the outer sleeve 135. It is, however, also within the intended scope of the present invention to insert the coil 120 within the outer sleeve 135 to form a unit together and thereafter insert the inner support tube 140 into the inner cavity formed by the coil 120 that forms a unit with the outer sleeve 135. Thus, the order of assembly of these three components (e.g., the inner support tube 140 (with the side port openings defined in the distal section or region thereof); the coil 120; and the outer sleeve 135) may be selected, as desired, and is within the intended scope of the prevent invention.

A straight mandrel is inserted in a longitudinal direction through the passageway of the inner support tube 140 after being assembled together with the coil 120 and outer sleeve 135. The straight mandrel is heated to a prescribed fusing temperature to cause the outer sleeve 135 material (e.g., polyether block amide (PEBA) or other thermoplastic polymer) to reflow over the outer surface of the inner support tube 140 (made of a thermoplastic polymer material that does not melt at that temperature such as polyether ether ketone (PEEK)), radially inward through the side port openings 165a-165c, and partially into (along the inner wall of) the passageway 143. Thus, in the areas where the outer sleeve material seeps into the passageway the inner diameter of the passageway of the inner support tube is reduced. The dimensions of the side port openings 165a-165c are selected to allow sufficient reflow of the material of the outer sleeve 135 to seep into the passageway 143 of the inner support tube 140 and create a controlled amount of friction force when directly physically contacting or directly engaging with the securement wire 150 threaded therethrough. By way of illustrative example, the preferred range of outer diameter of the mandrel is in a range of approximately 70%-approximately 80% of the inner diameter of the passageway of the inner support tube. In experimental testing, the outer diameter of the mandrel is 0.003 in. creating an intentional friction zone within a range of approximately 10 gF to approximately 20 gF to maintain the position of the securement wire in the delivery and detachment system during use.

In addition to the friction force resulting from the reduced or decreased inner diameter of the passageway 143 of the inner support tube 140 created by the reflow of the outer sleeve material through the side port openings into the passageway, an additional contribution to the friction force imposed on the securement wire 150 may be produced by the frictional characteristics of the reflow material itself of the outer sleeve upon contacting with the outer surface of the mandrel. In this regard, the mandrel used to reflow the outer sleeve material through the side port openings created in the inner support tube may be either coated (i.e., a mandrel coated with a lubricious coating) or non-coated (i.e., a mandrel not coated with a lubricious coating). In the case of a non-coated (free of any lubricious coating) mandrel the reflowed outer sleeve material adheres along the entire outer surface of the mandrel providing a predetermined amount of tacking force desirably contributing to the controlled friction force imposed on the outer surface of the securement wire. Even when using a mandrel coated with a lubricious material (e.g., Polytetrafluoroethylene (PTFE)), portions, sections, or regions of the outer surface of the mandrel exposed or lacking the coating will nevertheless exist producing patches in which a tacking force is produced. In the case of the coated mandrel, the tacking force is generated only in those random areas where the coating happens to be omitted, missing, or not present on the outer surface of the mandrel, whereas the tacking force produced when employing a non-coated mandrel extends substantially over the entire outer surface of the mandrel.

After the prescribed exposure time to the heat temperature has expired (for example, 420° F. for a period of 5 sec.-30 sec.) withdraw of the mandrel from the three-component assembly (outer sleeve 135, coil 120; and inner support tube 140) allows cooling and hardening of the material of the outer sleeve 135 that has seeped through the side port openings into the passageway 143 of the inner support tube 140. Next, the securement wire 143 secured at its distal end to a distal assembly comprising the detachment coil 125, proximal key 160 and implantable intravascular device 130 is threaded in a proximal direction through the passageway 143 of the three-component assembly (reflowed outer sleeve 130, coil 120, and inner support tube 140).

A main delivery tube 115 having a channel 113 defined in a longitudinal/axial direction therethrough is assembled to the proximal end of the thus assembled delivery and detachment system. Specifically, the proximal end of the inner support tube 140 extends in a proximal direction beyond the proximal end of the of the coil 120 and is sized to be telescopically receivable in the channel 113 of the main delivery tube 115. The threading of the securement wire 150 continues in a proximal direction through the channel 113 of the main delivery tube 115 and a lumen 170 of a proximal inner tube 145 whose distal end is received within the channel 113. A portion of the proximal end of the proximal inner tube 145 extends in a proximal direction relative to the proximal end of the main delivery tube 115. The proximal end of the securement wire that has been threaded in a proximal direction rough the lumen 170 of the proximal inner tube 145 and the channel 113 of the main delivery tube 115 is non-releasably secured (e.g., welded) 175 to the proximal end of the proximal inner tube 145.

In use, a catheter or microcatheter is navigated through the artery to the proximal side of the target site (e.g., aneurysm). Thereafter, using the assembled delivery and detachment system (as shown in FIG. 1) the implantable intravascular device 130 releasably secured to the distal end thereof is advanced through the catheter or microcatheter to the target site. During delivery of the implantable intravascular device 130 by the interventionalist (prior to deployment) undesirable shifting, movement or translation of the securement wire is prevented or minimized by intentionally imposing a controlled friction force on a radially outward surface along a distal section of the securement wire 150 where it directly physically contacts the reflowed material of the outer sleeve 135 that has seeped through the side port openings 165 of the inner support tube 120 and into the passageway 143 thereof. The amount of friction force imposed is sufficient to prevent or minimize shifting, movement or translation of the securement wire in the passageway during delivery able to be overcome only by application of sufficient axial force in a proximal direction on the securement wire when deploying (releasing) the implantable intravascular device from the delivery and detachment system to be precisely and accurately deposited at the target site in the artery.

Figure 5:
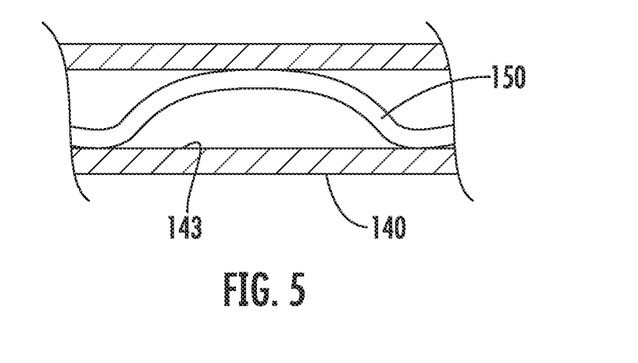
FIG. 5 is a partial longitudinal cut-away view of the inner support tube in an alternative embodiment in which the securement wire has multiple bends or kinks (e.g., trapezoidal in shape), each bend or kink in direct physical contact at associated points with the inner walls of the passageway of the inner support tube.

The design described above and illustrated narrows the inner diameter of the passageway defined in the inner support tube by reflow of the outer sleeve material through side port openings defined therein and into the passageway to intentionally narrow the inner diameter along those areas imposing a controlled friction force on the outer surface of the securement wire threaded therethrough. Other mechanical configurations to intentionally introduce a controlled friction force on the outer surface of the securement wire are contemplated and within the intended scope of the present invention. Rather than alter the structure of the inner support tube (e.g., creating the side port openings in and reducing the inner diameter of the passageway thereof) the design of the securement wire along a distal section thereof may be modified. In this regard, a bend or kink in the otherwise substantially linear may be made along a distal section of the securement wire to intentionally create one or more points/sections/areas/regions of direct physical contact between the securement wire 150 and the inner wall of the passageway 143 of the inner support tube 140. For instance, the securement wire 140' in FIG. 5 intentionally includes multiple bends or kinks configured as a trapezoidal shape establishing direct physical regions of contact of the securement wire with the inner wall of the passageway (approximately 180° radially from one another) resulting in the imposition of an intentional controlled friction force. Alternative configurations in the bending or kinking of the securement wire forming a variety of geometric shapes are contemplated and within the intended scope of the present invention. The number of, overall surface area, and/or spacing between points/sections/areas/regions of forced or intentional direct physical contact between the securement wire and the inner wall of the lumen of the inner support tube may be selected, as desired, to achieve a controlled intentional friction force on the securement wire when assembled within the delivery and detachment system. Once again keeping in mind that, on the one hand, the intentional controlled friction force imposed by the bent or kinked securement wire directly engaging with the inner wall of the passageway of the inner support tube is sufficient to prevent or minimize shifting, translation or movement of the securement wire during delivery of the implantable intravascular device. Yet, on the other hand, upon application of sufficient force in a proximal direction on the securement wire 140 the intentional controlled friction force is overcome releasing the implantable intravascular device 130 from the delivery and detachment system.

Regardless of the particular mechanical design of the way in which the assembled delivery and detachment system creates an intentional friction zone, the controlled amount of friction force imposed on the securement wire when assembled in the delivery and detachment system may be modified, as desired, to prevent or minimize shifting, translation, or movement of the securement wire during delivery and detachment of the implantable intravascular device, yet able to be overcome when sufficient force is applied in a proximal direction on the securement wire to release the implantable intravascular device. The present invention has been shown and described with respect to a delivery and detachment system loaded with an embolic coil during a coil embolization procedure in the treatment of an intracranial aneurysm. It is contemplated and within the intended scope of the present invention to utilize the present inventive delivery and detachment system for other types of implantable intravascular devices used in other endovascular treatment procedures.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A delivery and detachment system for an implantable intravascular device, the system comprising:

an inner support tube having a passageway extending in an axial direction from a proximal end to an opposite distal end; and a securement wire extending through the passageway of the inner support tube;

an intentional friction zone imposes a controlled friction force on the securement wire; the intentional friction zone is located anywhere between the distal end of the inner support tube and a midway point between the respective proximal and distal ends of the inner support tube;

an outer sleeve surrounding an outer surface of the inner support tube, wherein the outer sleeve is made of a reflowable material; wherein the inner support tube has defined therein at least one radially inward side port opening intersecting with the passageway; and the reflowable material of the outer sleeve is present in the at least one radially inward side port opening defined in the inner support tube and is present in the passageway of the inner support tube forming an associated point of direct physical contact with the securement wire.

2. The delivery and detachment system according to claim 1, further comprising a coil disposed between the inner support tube and the outer sleeve; the reflowable material of the outer sleeve is present through the coil.

3. The delivery and detachment system according to claim 1, wherein the securement wire is straight.

4. The delivery and detachment system according to claim 1, wherein the securement wire has at least one bend therein wherein each of the at least one bend is directly physically contacting the reflowable material of the outer sleeve disposed in the passageway of the inner support tube.

5. The system in accordance with claim 1, further comprising an implantable intravascular device releasably secured to a distal end of the delivery and detachment system via the securement wire.

6. The system in accordance with claim 1, further comprising:
a main delivery tube having a proximal end, an opposite distal end, and a channel extending axially therebetween; the proximal end of the inner support tube telescopically received in the channel at the distal end of the main delivery tube; and
a proximal retaining tube having a proximal end, an opposite distal end and a lumen extending in an axial direction therebetween; the securement wire extending through the lumen and secured to the proximal end of the proximal retaining tube; the distal end of the proximal retaining tube telescopically received in the proximal end of the main delivery tube.

7. A method for manufacture of a delivery and detachment system for an implantable intravascular device:
wherein the delivery and detachment system includes:
an inner support tube having a passageway extending in an axial direction from a proximal end to an opposite distal end; and
a securement wire extending through the passageway of the inner support tube;
an intentional friction zone imposes controlled friction force on the securement wire; the intentional friction zone located anywhere between the distal end of the inner support tube and a midway point between the respective proximal and distal ends of the inner support tube;
an outer sleeve surrounding an outer surface of the inner support tube, wherein the outer sleeve is made of a reflowable material;
wherein the inner support tube has defined therein at least one radially inward side port opening intersecting with the passageway; and
the reflowable material of the outer sleeve is present in the at least one radially inward side port opening defined in the inner support tube and is present in the passageway of the inner support tube forming an associated point of direct physical contact with the securement wire;
the method comprising the steps of:
providing the inner support tube having the passageway extending in the axial direction from the proximal end to the opposite distal end;
as the securement wire is being threaded through the passageway of the inner support tube, imposing on the securement wire the controlled friction force established within the intentional friction zone located anywhere between the distal end of the inner support tube and the midway point between the respective proximal and distal ends of the inner support tube;
creating the at least one radially inward side port opening in the inner support tube;
each of the at least one radially inward side port openings extending radially inward and intersecting with the passageway of the inner support tube;
assembling the outer sleeve made of the reflowable material about the outer surface of the inner support tube to create an assembly;
heating the assembly so the reflowable material of the outer sleeve seeps through the at least one radially inward side port opening into the passageway of the inner support tube creating the intentional friction zone;
wherein along the associated point the securement wire being in direct physical contact with the reflowable material of the outer sleeve present in the passageway of the inner support tube.

8. The method according to claim 7, further comprising a coil positioned radially between the inner support tube with the at least radially inward one side port opening created therein and the outer sleeve.

9. A method of using a delivery and detachment system for an implantable intravascular treatment device; the delivery and detachment system including an inner support tube having a passageway extending in an axial direction between a proximal end and an opposite distal end; and the delivery; and detachment system further including a securement wire extending through the passageway of the inner support tube; an intentional friction zone imposes a controlled friction force on the securement wire; the intentional friction zone is located anywhere between the distal end of the inner support tube and a midway point between the respective proximal and distal ends of the inner support tube; an outer sleeve surrounding an outer surface of the inner support tube, wherein the outer sleeve is made of a reflowable material; wherein the inner support tube has defined therein at least one radially inward side port opening intersecting with the passageway; and the reflowable material of the outer sleeve is present in the at least one radially inward side port opening defined in the inner support tube and is present in the passageway of the inner support tube forming an associated point of direct physical contact with the securement wire; the method comprising the steps of:
during delivery of the implantable intravascular treatment device to a target site, the imposed controlled friction force minimizing movement of the securement wire relative to the inner support tube; and
upon the implantable intravascular treatment device reaching the target site, applying a force in a proximal direction on the securement wire sufficient to exceed the imposed controlled friction force and releasing the implantable intravascular treatment device from the delivery and detachment system.

10. The method according to claim 9, wherein the delivery and detachment system further includes a coil disposed between the inner support tube and the outer sleeve.

11. The method according to claim 9, wherein the securement wire is straight.

12. The method according to claim 9, wherein the securement wire has at least one bend therein each bend directly physically contacting the reflowable material of the outer sleeve present in the passageway of the inner support tube.

* * * * *